United States Patent [19]
Manabe et al.

[11] Patent Number: 5,204,383
[45] Date of Patent: Apr. 20, 1993

[54] DENTAL ADHESIVES

[75] Inventors: Atsufumi Manabe; Kazuo Itoh; Sadao Wakumoto, all of Tokyo; Tokuji Hasegawa, Yokohama; Toshie Koike, Kawasaki, all of Japan

[73] Assignees: Kuraray Co., Ltd., Kurashiki; Mitsui Petrochemical Industries, Ltd., Tokyo, both of Japan

[21] Appl. No.: 892,725

[22] Filed: May 29, 1992

Related U.S. Application Data

[63] Continuation of Ser. No. 590,814, Oct. 1, 1990.

[30] Foreign Application Priority Data

Mar. 28, 1990 [JP] Japan .................................. 2-81768
Mar. 28, 1990 [JP] Japan .................................. 2-81769

[51] Int. Cl.$^5$ .......................... A61K 6/02; A61K 6/08
[52] U.S. Cl. .................................. 523/118; 433/226; 525/466; 526/273; 526/278; 526/317.1; 526/329.4; 526/320
[58] Field of Search ................ 523/118, 116; 525/466; 433/226; 526/273

[56] References Cited

U.S. PATENT DOCUMENTS 4,645,456  2/1987  James .............................. 433/217.1

Primary Examiner—Joseph L. Schofer
Assistant Examiner—Fred Zitomer
Attorney, Agent, or Firm—Sherman and Shalloway

[57] ABSTRACT

According to the present invention, a dental adhesive comprising glyceryl mono(meth)acrylate and a polymerizable monomer having at least one olefinic double bond and capable of copolymerizing with said glyceryl mono(meth)acrylate is provided.

4 Claims, No Drawings

DENTAL ADHESIVES

This application is a continuation of application Ser. No. 07/590,814, filed Oct. 1, 1990.

FIELD OF THE INVENTION

This invention relates to dental adhesives having excellent properties of bonding a tooth and a dental restorative material together, and having excellent properties of marginal sealing between the tooth and material thus bonded.

BACKGROUND OF THE INVENTION

In the field of dental goods and materials, there have recently been developed various adhesives having excellent adhesiveness to a tooth, especially to a dentinal portion thereof. Used as adhesive components in such adhesives as referred to above are polymerizable monomers having acid groups in the molecule. These polymerizable monomers which are known, per se, include (meth)acrylate monomers such as those having in the molecule phosphoric acid diester groups (Japanese Patent L-O-P Publn. No. 113089/1977), phosphoric acid monoester groups (Japanese Patent L-O-P Publn. No. 21607/1983), carboxyl group or acid anhydride groups (Japanese Patent L-O-P Publn. No. 11149/1979) and acid halide groups (Japanese Patent L-O-P Publn. No. 151607/1982).

However, even in the adhesives containing such adhesive monomers as mentioned above, a further improvement is desired in that when a dental restorative material (filling material, metal, etc.) is applied to a tooth, a further improved adhesion between the tooth and material is obtained and, moreover, no gap is formed in the marginal gap between the tooth and material thus united.

OBJECT OF THE INVENTION

The present invention has been made in view of the prior art as mentioned above, and an object of the invention is to provide dental adhesives which are excellent in adhesive properties and, in addition thereto, excellent in marginal sealing properties capable of inhibiting the formation of marginal gap between a tooth and a dental restorative material applied thereto.

SUMMARY OF THE INVENTION

The dental adhesives of the present invention are characterized by comprising glyceryl mono(meth)acrylate and a polymerizable monomer having at least one olefinic double bond and capable of copolymerizing with said glyceryl mono(meth)acrylate.

The dental adhesives of the invention as illustrated above may be in the form of a mixture containing glyceryl mono(meth)acrylate and a polymerizable monomer having at least one olefinic double bond and capable of copolymerizing with said glyceryl mono(meth)acrylate.

The dental adhesives of the invention mentioned above may also be in the form of at least two packs, one containing glyceryl mono(meth)acrylate, and at least the other containing a polymerizable monomer having at least one olefinic double bond and capable of copolymerizing with said glyceryl mono(meth)acrylate.

DETAILED DESCRIPTION OF THE INVENTION

The dental adhesives of the present invention comprise glyceryl mono(meth)acrylate and a polymerizable monomer copolymerizable with said glyceryl mono(meth)acrylate.

Glyceryl mono(meth)acrylate has two hydroxy groups in the molecule, and therefore the dental adhesives comprising glyceryl mono(meth)acrylate and a polymerizable monomer copolymerizable with said glyceryl mono(meth)acrylate have excellent adhesive properties and excellent marginal sealing properties capable of inhibiting the formation of marginal gap between a tooth and a dental restorative material.

Gyceryl mono(meth)acrylate include as isomers 1,3-dihydroxyisopropyl (meth)acrylate and 2,3-dihydroxypropyl (meth)acrylate, and 2,3-dihydroxypropyl (meth)acrylate is preferred in point of adhesive properties. Usually, methacrylate monomers are used more frequently than acrylate monomers.

The polymerizable monomer used in the invention includes (meth)acrylic acid esters, (meth)acrylamides, maleic acid esters, fumaric acid esters, vinyl esters such as vinyl acetate, styrene and derivatives thereof, and vinyl compounds such as acrylonitrile and acrolein. Of these monomers as exemplified above, particularly preferred are (meth)acrylic acid esters.

Exemplified as (meth)acrylic acid esters are methyl (meth)acrylate, 2-hydroxyethyl (meth)acrylate, ethylene glycol di(meth)acrylate, triethylene glycol di(meth)acrylate, neopentyl glycol di(meth)acrylate, 2,2-bis 4-(3-methacryloyloxy-2-hydroxy-propoxy)phenyl propane (Bis-GMA), trimethylolethane tri(meth)acrylate, pentaerythritol tetra(meth)acrylate and N,N-dimethylaminoethyl methacrylate.

Further, as the polymerizable monomers preferably used in the invention, there may be mentioned polymerizable acid monomers having at least one acid group selected from the group comprising

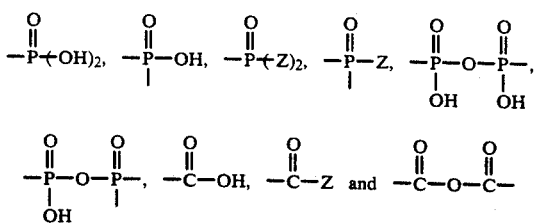

(in which Z represents halogen, and further the above-mentioned groups do not link to hydroxyl, halogen or

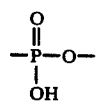

and at least one olefinic double bond.

As the polymerizable acid monomers as illustrated above, there may be used such compounds as will be exemplified below.

(i) The compounds having the group

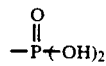
include those represented by the following formulas.
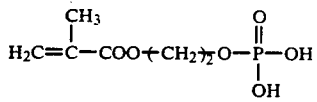
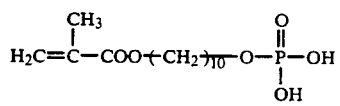
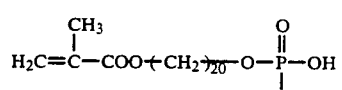
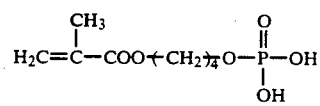
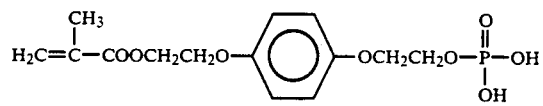
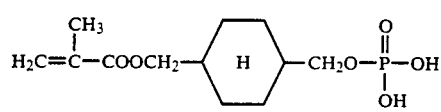
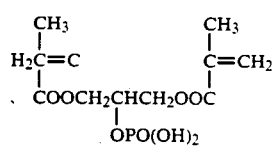
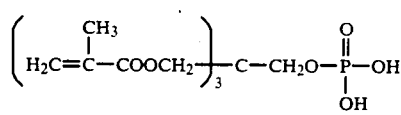
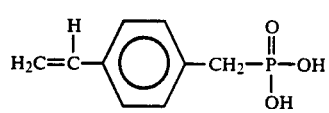
-continued
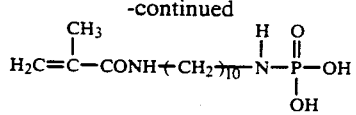
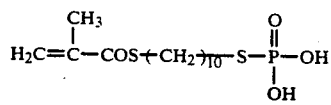
(ii) The compounds having the group
include those represented by the following formulas.
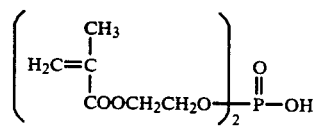
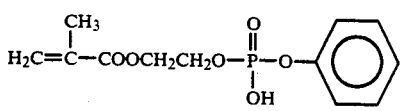
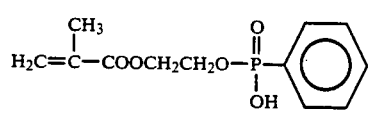
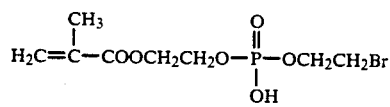
(iii) The compounds having the group
include those represented by the following formulas.
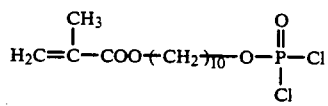  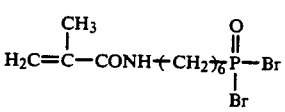
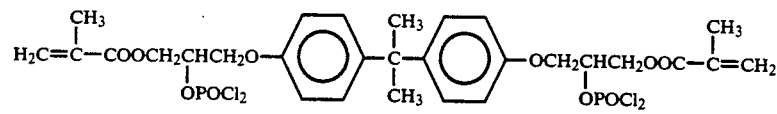
(iv) The compounds having the groups
include those represented by the following formulas.

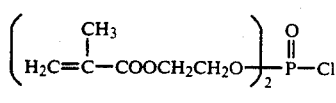 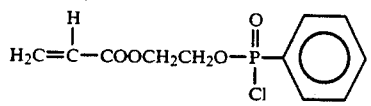

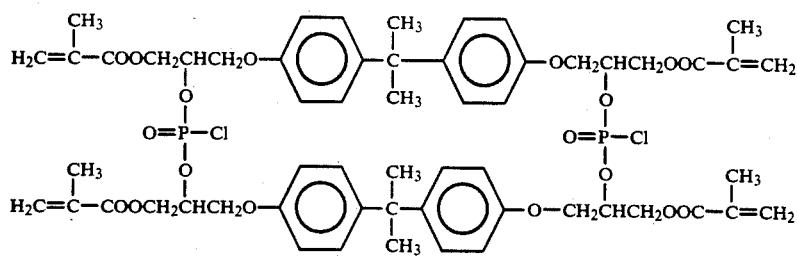

(v) The compounds having the group

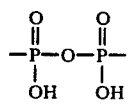

include those represented by the following formulas.

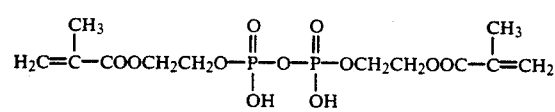

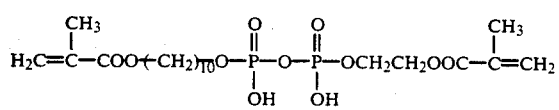

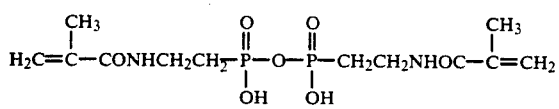

(vi) The compounds having the group

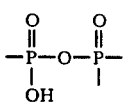

include that represented by the following formula.

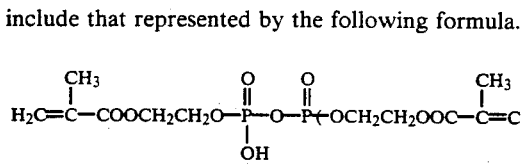

(vii) The compounds having the group

include those represented by the following formulas.

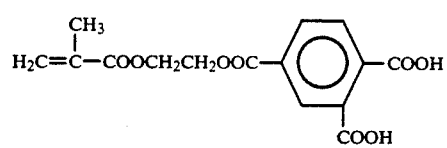

-continued

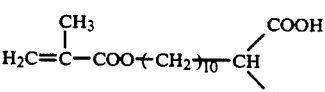

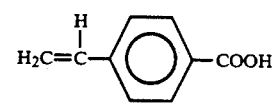

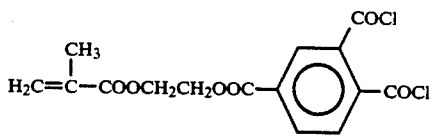

(viii) The compounds having the group

include that represented by the following formula.

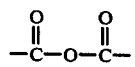

(IX) The compounds having the group

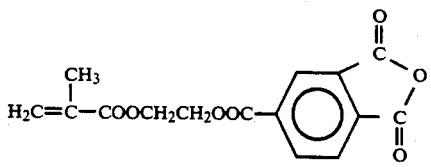

include those represented by the following formulas.

-continued

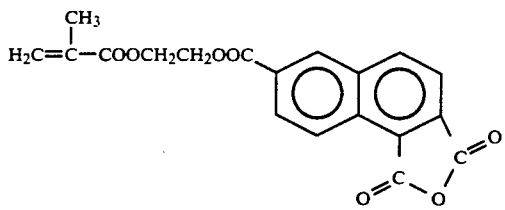

As mentioned above, the dental adhesives of the present invention comprise glyceryl mono(meth)acrylate and a polymerizable monomer, preferably a polymerizable acid monomer capable of copolymerizing with said glyceryl mono(meth)acrylate, and are used usually in the following form.

(1) The dental adhesive used is in the form of a system comprising a mixture of glyceryl mono(meth)acrylate and a polymerizable monomer, preferably a polymerizable acid monomer capable of copolymerizing with said glyceryl mono(meth)acrylate, or of the above-mentioned system to which a third component such as a solvent, filler or polymerization initiator has been added if necessary.

In the dental adhesives used in the above-mentioned form, the amount, based on the total weight of the adhesive, of glyceryl mono(meth)acrylate contained is 0.01-50% by weight, preferably 0.1-30% by weight, and similarly that of the polymerizable acid monomer contained is 0.01-50% by weight, preferably 0.1-30% by weight.

Because of a one-packtype formulation, the dental adhesives mentioned in the foregoing (1) are easy in handling in comparison with the dental adhesives as will be formulated in the undermentioned (2) and have no practical difficulties in respect to their storage stability.

The dental adhesives having the formulation of such mixture as mentioned above are used by applying them on a tooth, especially a dentin.

(2) The dental adhesive used is in the form of a system comprising a package containing a composition [A] in which glyceryl mono(meth)acrylate has been contained and a package containing a composition [B] in which a polymerizable monomer, preferably a polymerizable acid monomer capable of copolymerizing with said glyceryl mono(meth)acrylate has been added.

The dental adhesives having such a formulation as mentioned above are used in such a manner that the composition [A] is first applied on a tooth, especially a dentin, and the composition [B] is laminated by applied on the surface of the composition [A] thus coated.

The composition [A] contains glyceryl mono(meth)acrylate and a volatile organic solvent having a boiling point of below 200° C. at atmospheric pressure or water or mixtures thereof and if necessary, copolymerizable monomers, polymerization initiators, fillers, etc. The amount, based on the total weight of the composition [A], of glyceryl mono(meth)acrylate contained therein is 0.1-80% by weight, preferably 1-50% by weight, and similarly that of the polymerizable acid monomer contained is 0.01-50% by weight, preferably 0.1-30% by weight.

The composition [B] usually contains a polymerization initiator in addition to the above-mentioned polymerizable monomer, and if necessary, may contain a solvent, fillers, etc. Furthermore, the composition [B] may be formulated into a two-divided pack system.

The content in the composition [B] of the above-mentioned polymerizable monomer is 0.01-50% by weight, preferably 0.1-30% by weight. The weight proportion of the composition [A] to the composition [B] used in the dental adhesives is from 1:100 to 10:1, preferably from 1:10 to 2:1.

The solvent preferably used in the dental adhesives of the present invention includes volatile organic solvents having boiling point below 200 ° C. at atmospheric pressure, for example, alcohols such as methanol, ethanol, allyl alcohol, isopropanol and 1-octanol; ketones such as acetone, methyl ethyl ketone and phorone; ethers such as ethyl ether, 1,4-dioxane, diethylene glycol and diethyl ether; esters such as ethyl acetate, butyl acetate and 2-ethylhexyl acetate; and hydrocarbons such as hexane, undecane, toluene, xylene, methylene chloride, 1,2-dichloroethane and 1,1,2,2-tetrachloroethane, or water or mixtures thereof.

The polymerization initiator used in the dental adhesives of the dental adhesives of the invention includes benzoyl peroxide-aromatic tertiary amine systems, peroxides such as cumene hydroperoxide, tributyl borane, and aromatic sulfinic acid (or salts thereof) -aromatic secondary or tertiary amine-acylperoxide systems, and further includes photopolymerization initiators such as α-diketone (e.g. camphorquinone, diacetyl or benzyl) -reducing agent systems and benzoin methyl ether, etc.

The filler used in the adhesives of the invention includes inorganic fillers such as glass, quartz, hydroxyapatite, calcium carbonate, barium sulfate, aluminum oxide, titanium oxide and zirconium oxide, and polymer powders such as polymethyl methacrylate, polystyrene and polyvinyl chloride, etc.

The dental adhesives of the invention are used in the same manner as in the case of common dental adhesive. Namely the present dental adhesives are applied on a tooth, and then the dental restorative material such as a filling material, metal or the like is applied to the surface of the thus coated tooth.

EFFECT OF THE INVENTION

The dental adhesives of the present invention have excellent adhesive properties to a tooth, especially dentin and, at the same time, are excellent in properties of marginal sealing between the tooth and the dental restorative material applied thereto Accordingly, the present dental-adhesives are useful for various dental purposes wherein such effects as mentioned above are required, especially for restoring teeth suffering from caries including particularly cervical dentin.

The present invention is illustrated below in detail with reference to examples, but it should be construed that the invention is in no way limited to those examples.

EXAMPLE 1

A composition (A) comprising 35 parts by weight of 2,3-dihydroxypropyl methacrylate ( glyceryl mono(meth)acrylate and 65 parts by weight of water was applied to the flat surface of dentin of an extracted human tooth abraded with #1000 abrasive paper and treated with 0.5M aqueous EDTA solution, followed by air blowing. The flat surface of dentin thus applied was further coated with a commercially available dental adhesive [Clearfil New Bond containing 10-methacryloyloxydecyl dihydrogenphosphate (a polymerizable acid monomer), a product of Kuraray Co., Ltd.] followed by air blowing, and then placed with a commercially available composite resin (Clearfil F II, a product of Kuraray Co., Ltd. containing Bis-GMA, triethyleneglycol dimethacrylate and quartz filler) followed by air blowing. The thus treated tooth was immersed in water at 37° C. for 24 hours and then subjected to tensile bond strength test to obtain a tensile bond strength of 153 kg/cm².

EXAMPLE 2

In each of 10 extracted human molar teeth, an adamantine adjacent to a dentin was removed, the dentin thus exposed was then flatted with #1000 abrasive paper, and a cylindrical cavity of 3 mm in diameter and 1.5 mm in depth was formed on the flatted dentin. The cavity thus formed was then treated inside with 0.5M aqueous EDTA solution for 60 seconds, followed by water washing and then drying. Thereafter, the composition (A) used in Example 1 was applied to the whole inner wall of the cavity, followed by air blowing. The inner wall of the cavity was coated with Clearfil New Bond followed by air blowing, and the cavity was filled with Clearfil F II, followed by setting.

Immediately thereafter, the tooth thus treated was immersed in water at room temperature, and allowed to stand for 10 minutes. Thereafter, the filled portion of the cavity was mirror polished to expose the cavity verge, and an interfacial border between the cavity verge and the filling materials was observed by means of a optical microscope (NIKON, OPTIPHOTO×400) so as to ascertain whether a gap is formed or not. As the result, no gap was observed at all over the whole circumferential verge of all of 10 specimens, and a good bonded state was shown in every case.

EXAMPLE 3

Example 2 was repeated except that the cavity was filled with a commercially available composite resin (PhotoClearfil A, a product of Kuraray Co., Ltd. containing Bis-GMA, triethyleneglycol dimethylacrylate, quartz filler and photoinitiator) in place of Clearfil F II, and the composite resin was cured by irradiation with light for 40 seconds by means of a visible light irradiation equipment (QuickLight manufactured by Kuraray Co., Ltd.), followed by the same test as in Example 2. The results obtained were good, showing that the specimens in which no gap was observed at all in the whole marginal gap of the cavity were 9 cases out of 10.

EXAMPLE 4

Example 2 was repeated except that a composition comprising 35 parts by weight of 2,3-dihydroxypropyl methacrylate, 35 parts by weight of water and 30 parts by weight of ethanol was used in place of the composition (A), followed by the same test as in Example 2. The results obtained were good, showing that the specimens in which no gap was observed were 9 cases out of 10.

EXAMPLE 5

The flat surface of a dentine of extracted human tooth abraded with #1000 abrasive paper was treated with 0.5M aqueous EDTA solution for 60 seconds, followed by water washing and then drying. The flat surface thus treated was applied with the undermentioned composition (B), followed by irradiation with light for 20 seconds by means of a visible light irradiation equipment (Quicklight manufactured by Kuraray Co., Ltd.). Thereafter, the flat surface thus treated was placed with a commercially available photocuring composite resin (PhotoClearfil, a product of Kuraray Co., Ltd. containing Bis-GMA, triethyleneglycol dimethylacrylate, quartz filler and photoinitiator), and cured by irradiation with light from QuickLight for 40 seconds. The thus treated tooth was immersed in water at 37° C. for 24 hours, and was then subjected to tensile bond strength test to obtain a tensile bond strength of 141 kg/cm².

| Composition (B) | |
|---|---|
| 2,3-Dihydroxypropyl methacrylate | 30 parts by weight |
| Bis-GMA | 60 parts by weight |
| 10-Methacryloyloxydecyl dihydrogen phosphate | 10 parts by weight |
| Camphor quinone | 0.5 parts by weight |
| Ethyl N,N-dimethyl-p-aminobenzoate | 0.5 parts by weight |

EXAMPLE 6

In each of 10 extracted human molar teeth, an adamantine adjacent to a dentine was removed, the dentine thus exposed was then flattened with #1000 abrasive paper, and a cylinder cavity of 3 mm in diameter and 1.5 mm in depth was formed on the flattened dentine. The cavity thus formed was then treated inside with 0.5M aqueous EDTA solution for 60 seconds, followed by water washing and then drying. Thereafter, the composition (B) was applied to the whole inner wall of the cavity, followed by air blowing and then irradiating with light for 20 seconds by means of a visible light irradiation equipment (Quicklight manufactured by Kuraray Co., Ltd.). The cavity was filled with a commercially available composite resin (Photoclearfill A, a product of Kuraray Co., Ltd.), and cured by irradiation with light for 40 seconds, followed by setting.

Immediately thereafter, the tooth thus treated was immersed in water at room temperature, and allowed to stand for 10 minutes. thereafter, the filled portion of the cavity was mirror polished to expose the cavity verge, and an interfacial border between the cavity verge and the filler was observed by means of a light microscope (NIKON, OPTIPHOTO×400) so as to ascertain whether a clearance is formed or not.

The results obtained were the same as those obtained in Example 3.

EXAMPLES 7-12

In each of 10 extracted human molar teeth, an adamantine adjacent to a dentine was removed, the dentine thus exposed was then flattened with #1000 abrasive paper, and a cylindrical cavity of 3 mm in diameter and 1.5 mm in depth was formed on the flattened dentine. The cavity thus formed was then treated inside with 0.5M aqueous EDTA solution for 60 seconds, followed by water washing and then drying. Thereafter, the undermentioned composition (C) was applied to the whole inner wall of the cavity, followed by air blowing and then irradiating with light for 20 seconds by means of visible light irradiation equipment (Quicklight manufactured by Kuraray Co., Ltd.). The cavity was filled with a commercially available composite resin (Photoclearfill A, a product of Kuraray Co., Ltd.), and cured by irradiation with light for 40 seconds, followed by setting.

Immediately thereafter, the tooth thus treated was immersed in water at room temperature, and allowed to stand for 10 minutes. thereafter, the filled portion of the cavity was mirror polished to expose the cavity verge, and an interfacial border between the cavity verge and the filler was observed by means of a light microscope (NIKON, OPTIPHOTO×400) so as to ascertain whether a clearance is formed or not.

The results obtained were good as shown in Table 1.

| Composition (C) | |
|---|---|
| Triethylene glycol dimethacrylate | 30 parts by weight |
| Bis-GMA | 50 parts by weight |
| Polymerizable acid monomer (as disclosed in Table 1) | 20 parts by weight |
| Camphor quinone | 0.5 parts by weight |
| Ethyl N,N-dimethyl-p-aminobenzoate | 0.5 parts by weight |

TABLE 1

| Example | Polymerizable acid monomer | Number of specimens having no gap |
|---|---|---|
| 7 | $CH_2{=}C(CH_3){-}COO(CH_2)_{10}{-}O{-}P(={O})(OH)_2$ | 10 |
| 8 | $CH_2{=}C(CH_3){-}COO(CH_2)_{10}{-}O{-}P(={O})(Cl)_2$ | 9 |
| 9 | $CH_2{=}C(CH_3){-}COOCH_2CH_2O{-}P(={O})(OH){-}O{-}P(={O})(OH){-}OCH_2CH_2OOC{-}C(CH_3){=}CH_2$ | 9 |
| 10 | $CH_2{=}C(CH_3){-}COOCH_2CH_2OOC{-}C_6H_3(COOH)(COOH)$ | 10 |
| 11 | $CH_2{=}C(CH_3){-}COOCH_2CH_2OOC{-}C_6H_4{-}COCl$ | 9 |
| 12 | $CH_2{=}C(CH_3){-}COOCH_2CH_2OOC{-}C_6H_3{-}(phthalic anhydride)$ | 10 |

COMPARATIVE EXAMPLE 1

Example 1 was repeated except that only Bond was applied to the tooth without using the composition (A), followed by the same adhesion test as in Example 1. The tensile bond strength as measured was 102 kg/cm².

COMPARATIVE EXAMPLE 2

Example 2 was repeated except that only Clearfil New Bond was applied to the cavity without using the composition (A), followed by the same test as in Example 2. As the result, the specimens in which no gap was observed at all in the whole marginal gap were 6 cases out of 10.

COMPARATIVE EXAMPLE 3

Example 2 was repeated except that a composition comprising 35 parts by weight of 2-hydroxyethyl methacrylate and 65 parts by weight of water was applied to the cavity in place of the composition (A), followed by the same test as in Example 2. As the result, the specimens in which no gap was observed at all were 7 cases out of 10.

COMPARATIVE EXAMPLE 4

Example 5 was repeated except that the composition (B) containing propyl methacrylate in place of the 2,3-dihydroxypropyl methacrylate was used, followed by the same adhesion test as in Example 5. The tensile bond strength as measured was 75 kg/cm².

COMPARATIVE EXAMPLE 5

Example 6 was repeated except that the composition (B) containing propyl methacrylate in place of the 2,3-dihydroxypropyl methacrylate was used, followed by the same test as in Example 6. As the result, the specimens in which no gap was observed in the whole marginal gap were 4 cases out of 10.

What is claimed is:

1. A dental adhesive comprising glyceryl mono(meth)acrylate and a polymerizable monomer having at least one olefinic double bond and capable of copolymerizing with said glyceryl mono(meth)acrylate, wherein the polymerizable monomer is a polymerizable acid monomer having at least one olefinic double bond and at least one acid group selected from the group consisting of

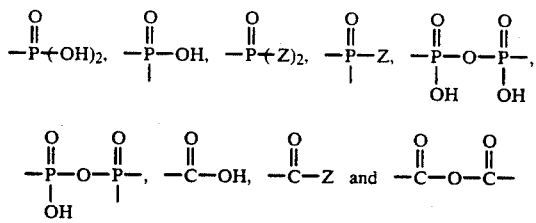

in which Z represents halogen, and further the above-mentioned groups do not link to hydroxyl, halogen or

and said

group links to an organic group having at least 8 carbon atoms.

2. The dental adhesive as claimed in claim 1 wherein said adhesive is in the form of said mixture of glyceryl mono(meth)acrylate and said polymerizable monomer having at least one olefinic double bond and capable of copolymerizing with said glyceryl mono(meth)acrylate.

3. A dental adhesive as claimed in claim 1 wherein said adhesive is in the form of at least two packs, one containing said glyceryl mono(meth)acrylate, and at least one other containing said polymerizable monomer having at least one olefinic double bond and capable of copolymerizing with said glyceryl mono(meth)acrylate.

4. The dental adhesive as claimed in claim 2 or 3 wherein said glyceryl mono(meth)acrylate is dissolved in a volatile organic solvent having a boiling point of below 200° C. at atmospheric pressure, water or a mixture thereof.

* * * * *